United States Patent [19]

Tanny

[11] Patent Number: 5,324,657
[45] Date of Patent: Jun. 28, 1994

[54] APPARATUS FOR PLANT CELL TISSUE CULTURE

[75] Inventor: Gerald B. Tanny, Rehovot, Israel

[73] Assignee: Osmotek Ltd., Israel

[21] Appl. No.: 49,537

[22] Filed: Apr. 20, 1993

[30] Foreign Application Priority Data

Apr. 21, 1992 [IL]  Israel .................................... 101659
Mar. 29, 1993 [IL]  Israel .................................... 105209

[51] Int. Cl.$^5$ .................... C12N 5/00; A01G 31/00; A01G 31/02; B32B 27/32
[52] U.S. Cl. .................... 435/240.45; 47/59; 47/62; 47/63; 47/64; 47/65; 428/220; 428/287; 435/284
[58] Field of Search .................. 47/63, 59, 62, 64, 65; 428/220, 287; 435/240.45, 284

[56] References Cited

U.S. PATENT DOCUMENTS

| | | | |
|---|---|---|---|
| 4,037,360 | 7/1977 | Farnsworth | 47/63 |
| 4,382,348 | 5/1983 | Kitsu et al. | 47/59 |
| 4,513,533 | 4/1985 | Gething et al. | 47/63 |
| 4,531,324 | 7/1985 | Yang et al. | 47/81 |
| 4,607,454 | 8/1986 | Koike | 47/63 |
| 5,126,189 | 6/1992 | Tanny et al. | 428/220 |

FOREIGN PATENT DOCUMENTS

2014836  9/1979  United Kingdom.

OTHER PUBLICATIONS

R. E. Young et al, "Approaching Mechanization of Plant Micropropagation", Trans. of the ASAE, vol. 34(1), Jan.-Feb., 1991, pp. 328-333.
R. M. Hamilton, H. Pederson, C. K. Chin, "Biotechniques", vol. 3, 1985, p. 96. (published results).

Primary Examiner—David T. Fox
Assistant Examiner—Elizabeth C. Kemmerer
Attorney, Agent, or Firm—Poms, Smith, Lande & Rose

[57] ABSTRACT

Apparatus for plant cell tissue culture including a plant growth enclosure having a bottom surface formed of a porous material, a buoyant element, separate from the plant growth enclosure and arranged to be placed thereunder in a body of liquid for supporting the plant growth enclosure, and spacer apparatus associated with at least one of the plant growth enclosure and the buoyant element for maintaining a predetermined separation between the buoyant element and the porous material.

25 Claims, 10 Drawing Sheets

APPARATUS FOR PLANT CELL TISSUE CULTURE

FIELD OF THE INVENTION

The present invention relates to plant cell tissue culture generally and more particularly to apparatus for plant cell tissue culture.

BACKGROUND OF THE INVENTION

Plant tissue culture involves growing all or part of a plant from a culture of parent cells. A number of techniques exist for plant tissue culture and include two general types: solid based cultures, in which cells are grown in a gel or membrane, and liquid cultures, in which the cells are free to float in the medium, in a manner similar to fermentation. In both cases, the objective is to make air, vitamins, minerals and hormones accessible to the growing cells or plants. The technique of preference depends on the specific plant, and the stage at which it is growing.

Membrane rafts, comprising hydrophilic microporous membranes sealed to a plastic base, have been described by prior art workers. The raft forms a floating platform on which to seed the cells for plant tissue growth. It comprises a frame to whose bottom perimeter a microporous membrane is sealed. The membrane serves as the bottom of the raft. Liquid and nutrients are meant to reach the cells growing on the membrane only through the pores. The frame prevents liquid from washing over the sides of the membrane. The design of the raft is meant to fit the growing vessel containing the liquid medium. Both square and round designs are known.

Medium contained in the liquid below the membrane reaches the cells by a combination of diffusion and bulk flow through the membrane pores and provides the cells with nutrients for growth. With some plants, substantial increases in the rate of plant growth can be achieved in comparison to growth on agar gels or other solid plant cell support systems. Reports of these results can be formed in the published results of Hamilton RM, Pederson H and Chin C-K, "Biotechniques", vol 3, page 96 (1985) and Young R. E., Hale A., Camper N. D., Keese R. J., and Adelberg J. W., "Transactions of the American Society for Agricultural Engineers", vol 34, pages 328-333 (1991).

Although diffusion to and from a growing cell is quite slow in a gel medium, it can be one or two orders of magnitude faster in a liquid. In the case of the membrane raft, the cell is supported on a solid surface, but the nutrients are transported via a liquid through the pores. The larger the pore size and the greater the number of pores in the membrane, the faster the rate of transport to and from the cells. Membrane rafts therefore have the potential advantage of combining the best features of liquid and solid culture techniques. However, the structure of the prior art rafts is far from optimal.

The current commercial raft design is literally that of a simple flat bottomed "raft", with four legs (Sigma Chemical Co., St. Louis, Mo.). The raft floats as a result of the volume of water displaced, and like any raft, depends on the impermeability of its base to keep liquid out so that it remains afloat. For this reason, the membrane used for the base is restricted to a film with very small pores, and a low hydraulic permeability. Even then, this must be coupled with a lightweight design for the remainder of the raft.

The weight of the raft provides a downwards pressure on the membrane through which water flows. If the flow rate is greater than the ability of the growing cells to use such medium, the cells will die or grow very poorly. In order to be successful, the prior art structure requires a very specific balance between the raft displacement weight and the membrane properties.

The reason for increased rates of growth are not clearly known. However, one may hypothesize that they are related to rates of transport of nutrients to the cells, and cell generated inhibitors or waste products away from the cells. The faster the rate of transport, the higher the effective concentration of growth nutrients, and the lower the concentration of species which inhibit the growth.

Rates of transport will be faster the larger the pores and the greater the surface area thereof. Conventional membranes and porous materials cannot be used in the conventional prior art structure because their hydraulic permeability is too high. Under the weight of the raft over a 24 hour period, conventional rafts either accumulate too much liquid on the surface of the raft or sink completely.

It has been proposed to construct a raft frame with hollow walls or walls made from a foamed material. These solutions reduce the surface area available for cell growth while reducing the depth of displacement of the raft and thus do not provide an acceptable solution.

As the plants grow, the weight of the raft increases with time. This increases the depth at which the raft is floating, as well as the pressure causing liquid to move through the membrane. Although this may sometimes be a desirable occurrence, the prior art structure does not enable control over when and to what extent the two results occur.

A second problem with the prior art raft structure relates to the later stages of plant growth and, more particularly to the development of the plant's root system. At the point at which the culture medium has been changed to cause expression of both the root system and the leaves, the ideal is for the roots to be continuously immersed in the culture medium, with the leaves above the liquid surface. At this stage it is also important for the plant to have mechanical support from the root system to physically support the upper portion of the plant.

Since rootlets cannot penetrate the pores of the membrane, they have nothing in which to anchor themselves to provide this support. The above-mentioned Young et al reference describes two frame membrane and netting devices, or sandwiches of membrane and netting which attempt to solve this problem. These comprise netting, with a regular array of openings large enough for the rootlets to grow through and anchor, placed on top of a microporous membrane. However, this requires peeling away the upper layer of growing plants, which are embedded in the netting, from the bottom layers. This approach is clumsy, expensive, and harmful to the plants as some shock is caused to the root system when the plants are separated.

The patent literature includes various examples of floating apparatus suitable for use in plane cell tissue culture.

U.S. Pat. NO. 4,037,360 describes raft apparatus for growing plants by means of water culture including a buoyant body arranged to float in a stable position on a nutrient solution. The buoyant member contains a generally vertically oriented channel which accommodates the step of a plant whose root system extends into the nutrient solution below the member. To facilitate seed germination, the channel may include a porous or absorptive partition which provides fluid communication by capillary action with a location on which a seed may germinate. During plant growth, buoyancy of the body is increased by adding auxiliary buoyancy apparatus.

U.S. Pat. No. 4,382,348 describes a soilless plant growing device which includes a fine mesh plate supported only at its periphery by a buoyant frame. The buoyancy of the apparatus is such that seeds are maintained at the surface of and in contact with the nutrient solution during germination, while the fine mesh allows roots to subsequently grow into the solution.

U.S. Pat. No. 4,513,533 describes a method of growing plants in an open trough on a sheet of buoyant hydrophobic material such as polystyrene in which are formed a regular pattern of large holes. The holes are covered by a connected grid of plant collars, which hold seedlings or a solid support medium in which a seed has germinated. The buoyancy of the sheet is such as to maintain the plants above the surface of the water in the trough throughout the growth cycle.

U.S. Pat. No. 4,607,454 describes a floating bed for hydroponically germinating seeds. The floating bed is floatable and is hydrophobic.

U.S. Pat. No. 4,531,324 describes a plant tissue culture device in which the cultures are maintained in culture wells on a porous wick which dips into a liquid medium and transports nutrients and water to the cultures.

U.K. Patent 2,014,836 describes a method for producing a stand of plants in which a buoyant inert base is covered with an absorbent material and floated on a trough of liquid. The ends of the absorbent material extend beyond the base and dip into the liquid, thereby transporting nutrients and water to seeds on the surface of the absorbent material.

SUMMARY OF THE INVENTION

The present invention seeks to provide improved plant growth apparatus.

There is thus provided in accordance with a preferred embodiment of the present invention apparatus for plant cell tissue culture including a plant growth enclosure having a bottom surface formed of a porous material, a buoyant element, separated from the plant growth enclosure and arranged to be placed thereunder in a body of liquid for supporting the plant growth enclosure, and spacer apparatus associated with at least one of the plant growth enclosure and the buoyant element for maintaining a predetermined separation between the buoyant element and the porous material.

In accordance with one embodiment of the invention, the spacer apparatus is integrally formed with the buoyant element. Alternatively, the spacer apparatus may be integrally formed with the enclosure. As a further alternative, the spacer apparatus may be partially defined by both the buoyant element and the enclosure.

Additionally in accordance with a preferred embodiment of the present invention there is provided a technique for plant growth including the steps of:

placing plant material in a plant growth enclosure assembly having a bottom surface formed of a porous material and a buoyant element;

placing the plant growth enclosure on a body of liquid for supporting the plant growth enclosure;

forcing the plant growth enclosure into the body of liquid such that the porous material is wetted; and allowing the plant growth enclosure to rise partially out of the body of liquid such that the porous material lies above an upper surface of the body of liquid but remains in contact with the upper surface of a meniscus of the body of liquid.

In accordance with a preferred embodiment of the present invention, the buoyant element is sufficiently buoyant to keep the porous material from being flooded at all stages of growth of the plant material in the plant growth enclosure.

There is also provided in accordance with a preferred embodiment of the present invention apparatus for plant cell tissue culture including a container for plant tissues including a frame defining a base and side wall apparatus, a porous material arranged at the base and containing a multiplicity of pores allowing the free diffusive flow of water and other dissolved species, and flotation apparatus associated with the frame and being operative such that absent the application of an external force, and when the porous material is not wetted, the container will float on an aqueous surface without the porous material touching the surface, and when the porous material is wetted, the porous material base of the device remains in fluid communication with the aqueous surface.

In accordance with a preferred embodiment of the present invention the container and flotation apparatus are constructed such that when the porous material is wetted, a force in excess of 0.01 dynes/sq.cm. is required in order to lift the base out of fluid engagement from the surface of tissue culture medium.

Further in accordance with a preferred embodiment of the present invention there is also provided divider apparatus disposed to divide the container into a plurality of cells, each communicating with a portion of the porous material and each being suitable for growing a single plant.

Preferably the flotation apparatus is removably attached to the frame.

In accordance with a preferred embodiment of the present invention the porous material includes a microporous polyolefin film of largest estimated pore size between 0.2 and 0.5 microns. Additionally the porous material comprises a nonwoven fabric characterized by an air flow of 11-31 Gurley seconds.

Preferably the nonwoven fabric has been uniformly needlepunched to produce a multiplicity of pores whose pore size lies between 25 microns and 2000 microns.

In accordance with a preferred embodiment of the present invention, the porous material contains a multiplicity of bores uniformly distributed over the surface, whose pore size distribution lies in the range between 0.02 microns and 10 microns.

Further in accordance with a preferred embodiment of the present invention, the porous material is characterized by a bimodal distribution of pores uniformly divided over the surface, whose lower pore size distribution lies in the range between 0.02 microns and 10 microns, and with a second distribution lying between 11 microns and 2000 microns.

Preferably the porous material also contains a multiplicity of pores uniformly distributed over the surface, whose pore size distribution lies in the range between 0.02 microns and 10 microns, and whose surface contains an additional multiplicity of pores lying in the range of 25 microns to 2000 microns, only on those portions of the surface corresponding to the cells.

In accordance with a preferred embodiment of the present invention, the porous material contains perforations which are congruent with the divider apparatus.

Preferably the divider apparatus defines sharp edges on their face adjacent to the porous material, for cutting the porous material upon application of sufficient force.

Additionally in accordance with a preferred embodiment of the present invention there is provided a method of variably adjusting the amount of fluid fed to plant cells growing on the porous material of any of the preceding claims via adjustment of (a) the flotation force which is in excess of the original displacement weight of the raft and (b) the hydraulic permeability of the porous material.

For example, a quantity of a given plant tissue to be cultured on the raft has an initial weight of x grams, and it is advantageous that the tissue is in direct contact with y grams per day of liquid nutrient, after it has grown to a weight of approximately 2x.

The area of the porous material of the raft to be used is chosen such that its force of adhesion is at least x. The flotation apparatus is designed to have an excess flotation force (total flotation less the weight of the raft) of x. Thus at the points that the weight of the growing tissue reaches 2 x, the rat is applying a pressure equal to the weight x divided by the raft area. Since the pressure, area, and flow rate, y grams per day, are all defined, the required hydraulic permeability is calculated for an appropriate porous material.

In accordance with a preferred embodiment of the present invention there is provided flotation apparatus similar to that of a catamaran, below the porous material. This provides an upward displacement which is in excess of the weight of the raft and its initial cell contents, such that the raft initially floats with the porous surface above the liquid surface. By making the excess displacement force less than the force required to remove the wetted porous surface from the liquid surface, the raft will float in direct contact with the surface only after it is pressed into contact with the liquid.

An examination of the force balance indicates that the meniscus of the liquid/porous material interface is above that of the remainder of the liquid. Thus the direction of any liquid flow is out of the raft, rather then into it as in the prior art. Membranes which would cause a prior art raft to quickly sink can be used in the present invention.

Apart from simply broadening the number of useful materials available for use in preparing rafts, the present invention enables use of membranes with larger pore sizes thus improving the rates of transport of both nutrients and plant generated toxins. This results in increased rates of growth, and healthier plants.

If some of the pores are in excess of 10 microns, the raft can be effectively used for the growth stage at which rootlets are allowed to develop. The rootlets can penetrate the porous material and anchor into it, while gaining access to the liquid medium below.

This feature of the invention makes it specifically useful for mechanization of the tissue culture process. By making these large pores or apertures only in predetermined locations, the plants can be easily separated for planting. The separation can be aided by a precut pattern of lines along which the porous material can be torn. This avoids any damage to the roots of the plants, and the piece of porous material in which the roots are embedded remains with the plant.

According to a preferred embodiment of the invention there is provided a floating support system for the growth of plant cells or micropropagules using liquid nutrient culture techniques.

The system comprises an open container for growing plant tissue, whose side surfaces, or frame, forms a closed space, and whose bottom surface is composed of a water wettable porous material capable of physically supporting the plant tissue to be cultured, and which allows the transport of water and nutrients. The bottom surface should be characterized by a wetting energy such that the force to remove 1 square centimeter of material from the surface of water is at least equal to 0.01 grams. The bottom is hermetically sealed to the frame, and liquid can enter the container only through the pores in the bottom surface. Flotation pontoons are located exterior to the container, beneath the porous material, and attached to extensions of the frame. In the specification, the container and pontoons will be referred to jointly as a raft.

The displacement force of the flotation pontoons is such that it is less than, or at most equal to, the combined weight of the raft plus its initial charge of plant tissue, plus the force required to remove the entire porous bottom from the surface of the liquid culture medium to be used.

Operation of the system preferably requires that the raft be placed with its pontoons resting in liquid nutrient medium appropriate for the tissue to be cultured. After plant tissue is placed on the porous bottom, the raft continues to float with the porous bottom out of contact with the liquid surface. By the application of a downward force to the frame of the raft the porous bottom is brought into contact with the liquid, and the raft remains floating on the surface by virtue of the interfacial forces between the porous bottom and the liquid.

The geometry of the system is determined principally by the requirements that it fit within the desired growth chamber containing the liquid medium and that it have appropriate clearances from the walls thereof to enable the raft to float freely. To maintain its hydraulic stability, the raft should possess at least one plane of symmetry.

Thus, in one embodiment, the raft is rectangular or square, with a single flotation pontoon attached to the frame at each of two opposing faces. In a second embodiment the frame of the raft is circular, and the pontoon is either a single element or is formed in multiple sections arranged about the frame perimeter. In this case, the extensions, which attach the frame to the pontoons, should have openings just below the porous bottom. The purpose of the openings is to allow air to escape when the downward force is applied to the frame of the raft, and to avoid entrapping air which would prevent the porous bottom from touching the liquid surface.

Another embodiment differs from the above-described embodiments in that divider elements reston the upper surface of the porous bottom such that they create a checkerboard pattern of specific locations for culturing individual plants. A further embodiment is similar to the foregoing, differing only in that the porous bottom at the center of the specific locations possesses a minority of pores or apertures large enough to allow penetration of rootlets, and a majority of pores or apertures which do not. In this way, the plants are forced to grow with their roots at well defined locations, which is important to the ease of their later separation, without damage to the plants.

Yet a further embodiment is similar to the preceding embodiment, differing only in that the porous bottom contains perforations congruent with the pattern of the divider elements. The perforations are of a size and density which makes it possible at the end of the culturing process to easily tear or break the porous bottom into sections each containing a single plant.

The divider elements may be constructed to be sharp, so as to cut the porous bottom into individual sections upon application of sufficient force.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
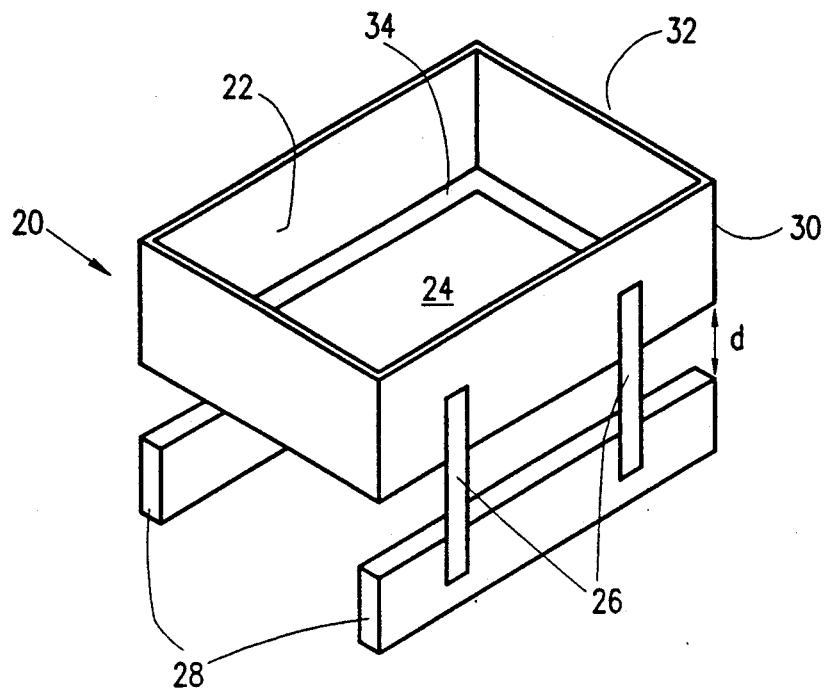
FIG. 1 is a three dimensional perspective of a rectangular embodiment of the raft system of the present invention.

Throughout the description which follows, identical elements have been given like index numerals. Reference is first made to FIG. 1 wherein a rectangular embodiment of the present invention is illustrated in complete form. The raft comprises an open container 20, with walls formed by a frame 22, and a porous bottom 24, made from a wettable porous film, fabric, mesh, or laminate of such elements, and which has been sealed to the bottom perimeter of frame 22 in liquid tight fashion so that liquid can only enter container 20 through the pores of porous bottom 24. Attached to the frame 22, at two opposite faces are struts 26, to which are attached flotation pontoons 28.

The lateral dimensions of the frame 22 are determined by the vessel in which the plants will be grown. The frame height 30, is the minimum necessary to keep liquid from spilling into the container 20 when the plants have grown to a weight in excess of the flotation provided by the pontoons. The thickness of the frame 32, is guided by considerations of maximization of the enclosed porous material surface available for growing, minimization of the weight (and cost), and provision of a surface for sealing the porous bottom 24 to the frame. For this reason, the bottom edge of the frame 22 may be given a lip 34, extending into the enclosed area, to minimize the overall frame thickness 32, but provide adequate seal area.

Frame 22 lends itself well to being molded of a plastic material which can withstand multiple sterilization by gamma radiation or by autoclaving in steam at 120 degrees Celsius for 20 minutes. For example, polyethylene is excellent for multiple sterilization by gamma radiation, while polypropylene is suitable for sterilization in an autoclave. Both materials are inert and do not contain materials which are phytotoxic.

The first embodiment is preferable for the stage of plant tissue culture known as multiplication, in which a smooth uniform surface is desirable. The porous bottom 24 can be made from any water wettable, uniformly porous material possessing pores in the pore size range of 0.02 to 2 microns, and which requires a force of 0.01 grams or more per square centimeter of material to be removed from the surface of the liquid. This includes, but is not limited to, porous plastic films, foams, paper, ceramics, metal foils, and nonwovens from synthetic or natural fibers.

The preferred pore size range for porous bottom 24 is 0.2 to 2 microns, and microporous films or nonwoven fabrics made from polyethylene or polypropylene or their mixture are preferable due to their sterilization properties and ease of welding to the frame. Since transport properties of the film are dependent on the total porosity, materials with a uniform distribution of pores and a fractional surface porosity of 0.3 or greater will be preferred.

A specific example of a porous polypropylene film available in this pore size range is that manufactured by Hoechst Celanese, Charlotte, N.C., under the trade name CELCARD. A specific example of a polyethylene nonwoven fabric of suitable pore size range is TYVEK style 1059B, DuPont company, Wilmington, Del. In both cases the materials must be made wettable by incorporation of a nontoxic wetting agent, such as L-77, Union Carbide, N.Y.

Numerous techniques are known in the art for sealing the porous bottom 24 to the frame, and these include adhesives, heat sealing, ultrasonic sound, r.f. welding, and insert molding. The method best suited to the system depends on considerations such as cost, nature of the materials chosen, and sterilization requirements, all of which are well known in the art.

The design and location of the struts 26 and pontoons 28 is guided by considerations of weight, and maximization of the growing area within the sterile container in which the raft and liquid medium are placed. If the struts are made as thin as possible, and the pontoons are placed directly below the porous material surface, as in FIG. 1, the raft can approach the walls of the vessel with a minimum distance. This maximizes growing area, an issue of significant economic importance.

The struts 26 need not be permanently adhered or welded to the frame 22, or to the pontoons 28 but can be individually fabricated and connected with snap fixtures, or molded sockets as is well known in the art. In addition, the pontoons 28 need not be in two sections, but could be a single slab as illustrated by pontoon 28 in FIG. 2.

The distance, d, of the pontoons from the porous bottom 24 can be important, because it could trap air and prevent liquid from reaching the porous bottom 24. Its value depends on the sensitivity of the plants being grown and the porous bottom 24 used. If porous bottom 24 wicks fluid sufficiently fast and the plant use is relatively low, air bubbles below the porous bottom 24 may be allowable. However, the preferred embodiment is likely one with a value of d which is 1 mm or more.

Figure 3:
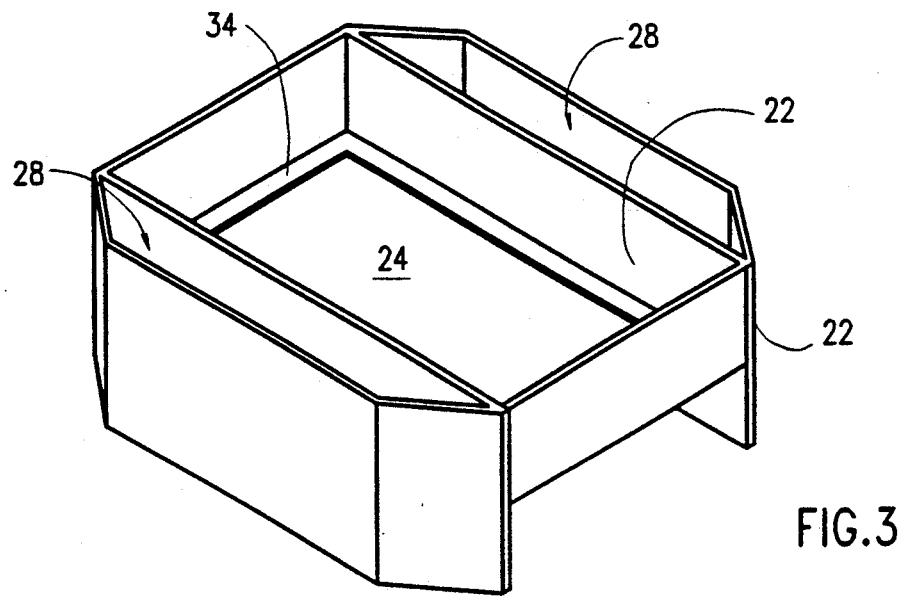
FIG. 3 is a view of yet another embodiment of pontoons useful in the present invention.

If maximization of growing area is not a consideration, then the struts 26 an pontoons 28 may be incorporated into an extension of two of the faces of the frame 22 illustrated in FIG. 3. Two parallel walls of the frame are extended below the liquid level to become part of hollow elements forming pontoons 28.

Figure 4:
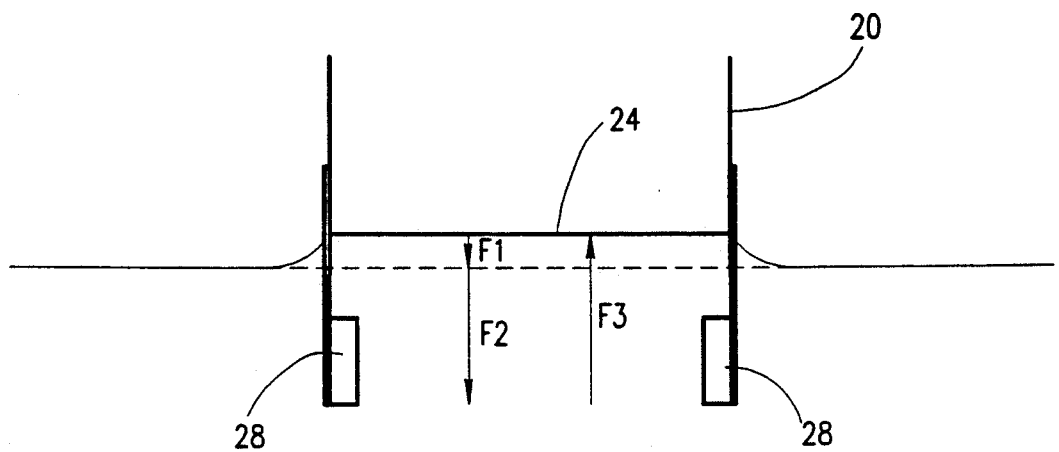
FIG. 4 is a schematic diagram illustrating the force balance maintaining the raft of the present invention at the surface of the liquid.

The displacement volume of the flotation pontoons is a critical aspect of the operation of the present invention. A force balance diagram, illustrated in FIG. 4, is useful to understand this point. It also serves to provide a useful contrast to the previous art.

Let F1 equal the downward force exerted by the weight of the raft, and F3 equal the upward force equal to the net weight of the volume of water displaced, Vp, less the weight of the pontoons. Let D equal the distance from the original surface of the liquid which the porous bottom 24 achieves at any time t. Our convention will be that values of D above the surface are negative, and below the surface positive, since the usual case is for boats or rafts to sink into the liquid.

$$F3 = (Vp \times 0.98 - \text{weight of pontoons}) \quad (1)$$

In the conventional art with no pontoons, the raft or boat, sinks to distance D in which the following equation holds:

$$F1 = D \times A \times \text{density of liquid} \quad (2)$$

where A is area of the raft, and F1 equals the weight of the container 20 plus the initial charge of plant tissue.

Pontoons with a displacement greater than the weight of the raft (i.e. $-F3 > F1$) would normally cause the device to float with its base out of the liquid. For cell culture, this design should therefore be unacceptable, since the cells must derive their sustenance from contact with the liquid medium through the porous bottom 24.

However, a very significant elastic force, F2, can exist between the porous bottom 24 and the liquid. Its magnitude depends on the lift distance, according to the equation:

$$F2 = -K \times D1 \times A \quad (3)$$

where K is a constant dependent on the interfacial energy of the porous bottom 24 and the liquid, with dimensions dynes/cc, A is surface area, and D1 is the distance by which the meniscus is raised above the surface layer of the liquid.

This additional elastic force provides the force balance at the surface illustrated in FIG. 4, once the porous bottom 24 has been forced into contact with the liquid by the application of some external force. As a result of the new force balance, the porous bottom 24 remains in constant contact with the liquid, even after the external force has been removed.

Figure 5:
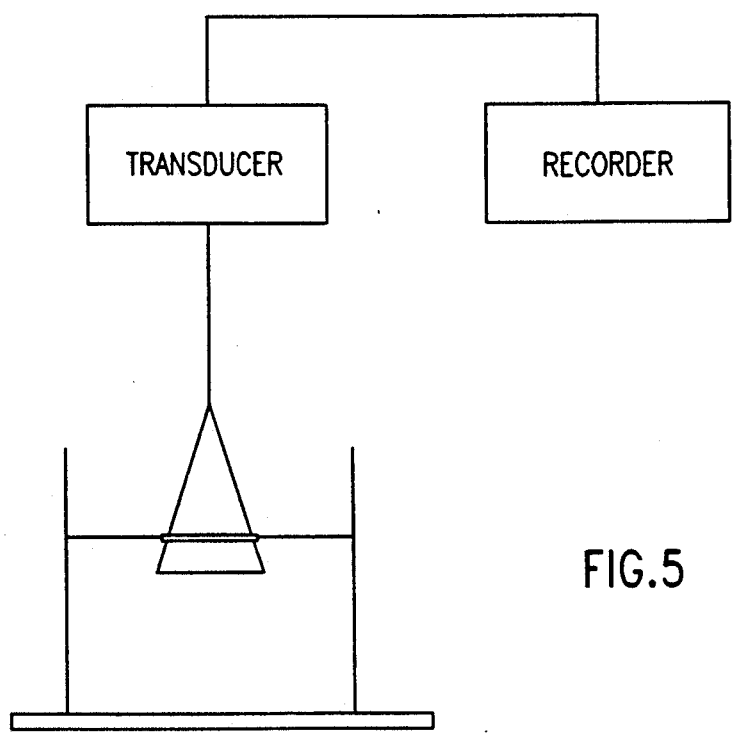
FIG. 5 is a schematic of the experimental apparatus used to measure the force per unit area required to remove porous materials from the surface of water.
Figure 6:
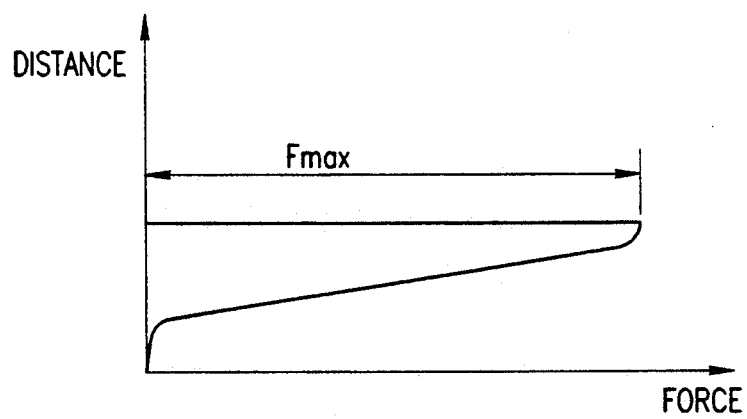
FIG. 6 is a typical experimental result of the measurement of the force per unit area required to remove porous materials from the surface of water.

Force F2 is measured with a transducer to which a platinum ring is suspended. The ring serves to support a 25 mm circle of porous bottom 24 material, which can be raised or lowered into the liquid below, as illustrated in FIG. 5. The porous bottom 24 sample material is allowed to just float on the surface of the water, and then the ring slowly lifts the porous bottom 24 material from the interface as the cup is lowered. The resultant force is recorded as an electrical output as illustrated in FIG. 6.

The magnitude of the forces necessary to remove the porous bottom 24 material from the surface, Fmax, is shown in Table I for different material.

Thus the maximum volume permitted for the pontoons is derived from the equation:

$$F\text{max} + F1 = -F3 = (Vp \times 0.98 - \text{weight of pontoons}) \quad (4)$$

Thus, if the force of additional flotation is restricted to just less than the elastic force between the liquid surface and the porous bottom 24, the porous bottom 24 continues to float without an upward hydraulic flow until the weight of the plant growth exceeds Fmax. This can be advantageous, because at a later stage in their development it may be desirable to supply the plants with more fluid. At the point that Fmax is exceeded, the level of the raft will sink and liquid will be forced through the porous bottom 24. By designing Vp to be equal to the weight of raft plus that of the grown plants at the time more fluid is desirable, the growth of the plants can be optimized.

The pontoons lend themselves well to be fabricated from a solid plastic foam of low density, or with a thin solid plastic wall and hollow interior. The choice depends only on the preferred method of manufacture and the type of sterilization to be used. For steam sterilization, the latter may be preferable due to its mechanical strength.

TABLE I

| Force required to remove various microporous membranes from the surface of water | |
|---|---|
| Membrane Type | Fmax (g/square cm) |
| Polysulphone, 0.45 micron | 0.53 |
| Polysulphone, 0.2 micron | 0.39 |
| Polypropylene. 0.45 micron (made wettable with surfactant) | 0.41 |

Figure 2:
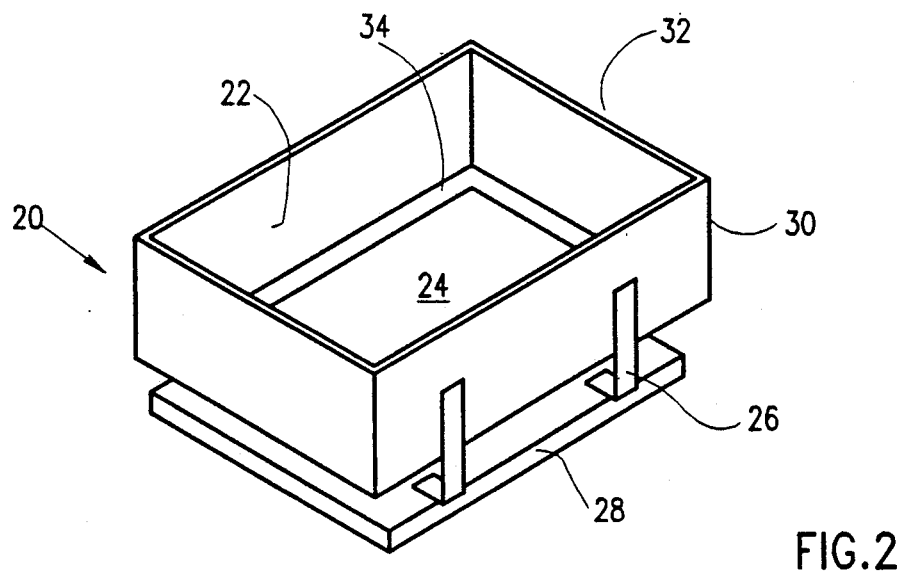
FIG. 2 is view of another embodiment of pontoons useful in the present invention.
Figure 7:
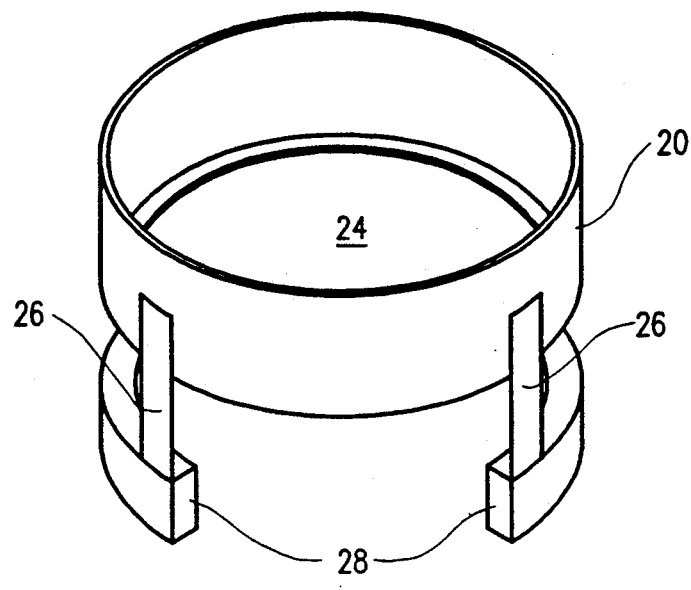
FIG. 7 is a three dimensional perspective view of a circular embodiment of the raft system of the present invention.
Figure 8B:
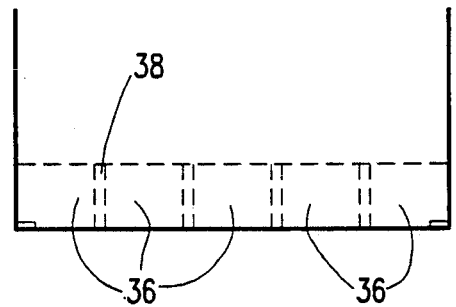
FIG. 8B is a cross sectional view, of divider elements resting on the porous material of the present invention.
Figure 8A:
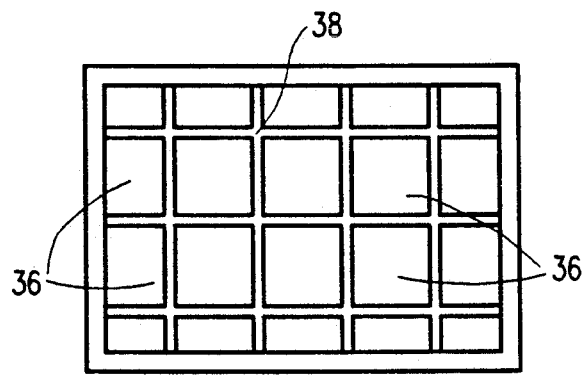
FIG. 8A is a top plan view.

The embodiments of the rafts illustrated in FIGS. 1 and 2 are rectangular or square, because the plant growth container for the liquid medium chosen is of this design. Circular designs are suitable for circular jars which are also used as plant growth containers, and such an embodiment is illustrated in FIG. 7. The surface of the porous bottom 24 may also be subdivided into a plurality of individual cells 36 each containing a single plant, by divider elements 38, as illustrated in FIGS. 8A and 8B.

The embodiments illustrated in FIG. 1 and 7 are preferably for the "multiplication" stages of tissue culture, in which root systems are not yet expressed. For the stage in which roots are generated, it is very useful for the porous bottom 24 to have pores or apertures which are large enough for plant rootlets to penetrate through the porous bottom 24. The root system is thereby immersed in liquid, while the upper portion of the plantlet is mechanically anchored. This embodiment is also preferred when the harvested material is the root of the plant.

Figure 9:
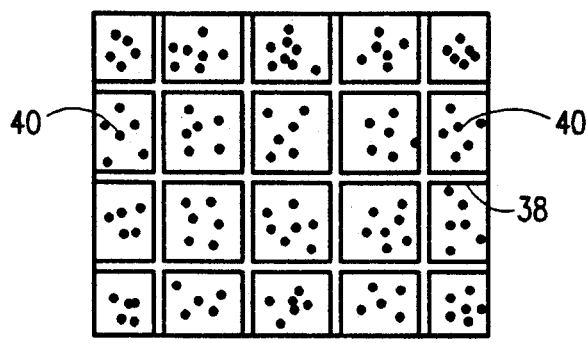
FIG. 9 is a top plan view of another embodiment of porous material and divider elements useful in the present invention.

For this application it is possible to choose a material for porous bottom 24 which has a random pore size distribution over the surface, with pores large enough to be penetrated by the finest rootlets, which are usually about 10 microns in diameter. However, a preferable choice is one in which the pores large enough for root penetration are at well defined locations. This will simplify the process of later separating the plants without causing any damage or trauma which would reduce their ability to survive rooting in soil when they are transferred. Thus the embodiment illustrated in FIG. 9 is substantially identical to FIGS. 8A and 8B, except that a number of large pores 40, of pore size range between 10 microns and 1 mm have been made in the porous bottom 24 in the middle area of cells 36. The use of a needle punched film or nonwoven fabric is a preferred for this embodiment, since the density, size and location of the large pores can be easily controlled.

Figure 10:
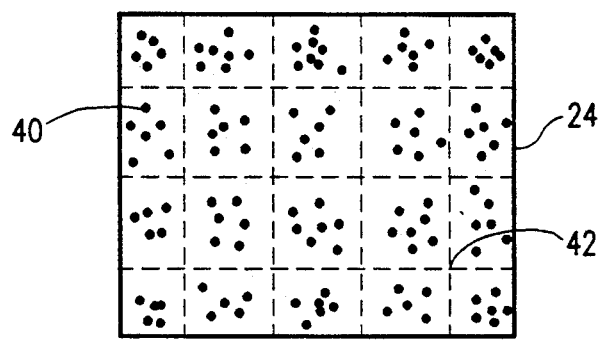
FIG. 10 is a top plan view of yet another embodiment of the porous material of the present invention.

Another embodiment of the porous bottom 24 of the present invention is illustrated in FIG. 10, in which the material of the porous bottom 24 has been given a pattern of perforations 42 which are congruent with the pattern of divider elements 38 of FIG. 9. This pattern of perforations makes it possible to later tear the porous bottom 24 and separate the plants without damage to the roots.

Figure 11:
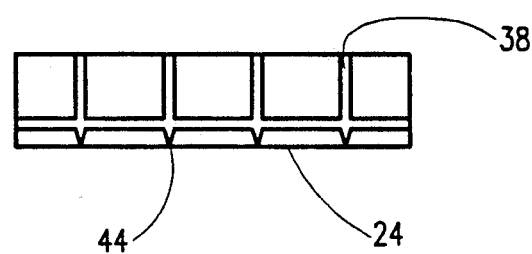
FIG. 11 is a cross sectional view of another embodiment of the divider elements and porous material of the present invention.

Another embodiment of the present invention is substantially identical to FIG. 9, except that the divider elements 38, illustrated in FIG. 11, have been given a razor sharp knife-edge 44, such that when sufficient force is applied, porous bottom 24 will be cut into pieces the size of cells 36. In this embodiment, porous bottom 24 is preferably made of a plastic film, paper or nonwoven fabric.

EXAMPLE 1

A membrane raft 10 cm ×10 cm was fabricated by attaching a 0.2 micron pore size polyolefin microporous membrane to the bottom of a polypropylene frame 1.5 cm high and 0.2 cm thick. The weight of the membrane and frame was 13.6 g. No pontoons for flotation were attached. The membrane had a treatment with a surfactant which rendered it wettable by water, and the raft floated initially with a displacement depth of approximately 2-3 mm in the water. After 48 hours, the volume of the raft was completely filled with water.

EXAMPLE 2

To the raft of example 1, square pontoons fabricated from polyethylene foam were attached with struts 3 cm long. The pontoons gave a total displacement of 26 g of water. The raft floated initially with the membrane several millimeters above the surface of the water. Upon application of sufficient force to cause immersion of the membrane, and movement of the raft to displace trapped air bubbles, the catamaran remained in continuous contact with the surface for more than 18 days. During this time it did not accumulate any liquid on its surface.

EXAMPLE 3

The catamaran raft design of example 2 was used to grow banana plants from cell culture. Twenty rafts were prepared and compared to a like number of agar controls. Both the rate of growth and the quality of plants produced on the catamaran was superior to the agar control. One raft which had a mechanical split in the membrane showed no ill effects of the tear, and growth was identical to the remainder of the plants.

EXAMPLE 4

The raft design of example 2 was fabricated with a porous material composed of mixed polyolefin fibers, which had been spun bonded into a nonwoven fabric, calendered and needle punched, (commercial name, TYVEK, style 1621, Dupont Corp.), to yield a bimodal pore size distribution. The small pore size distribution is estimated to mostly lie in the range of 0.5-5.0 microns, while the large pore size distribution created by needlepunching is in the range of 30-100 microns. The porous material was rendered hydrophilic by treatment with a surfactant. After the raft was pressed into contact with the water surface, it adhered to the surface without the continued application of additional force and continued to float without the accumulation of fluid on its surface even after 96 hours.

EXAMPLE 5

The following is an example of the method to modify raft design to adjust the amount of fluid fed to plant cells:

Growth of an initial charge of 10 grams of plant tissue per raft is desired. After the plant tissue weight reaches 20 grams, a liquid flow of 0.5 cc per day is optimal.

Assume a minimum value of $F_{max}$ is 0.2 grams/sq.cm exists for all porous materials available. An area of 55 square cm. will provide the necessary surface adhesion. If the weight of the frame and pontoons is 25 grams, then pontoons with 45 grams of flotation force are necessary (weight of raft+initial charge of plant tissue). A porous material with a hydraulic permeability of 0.00058 cc/square-cm/atmosphere/sec is chosen as the porous material bottom.

Figure 12:
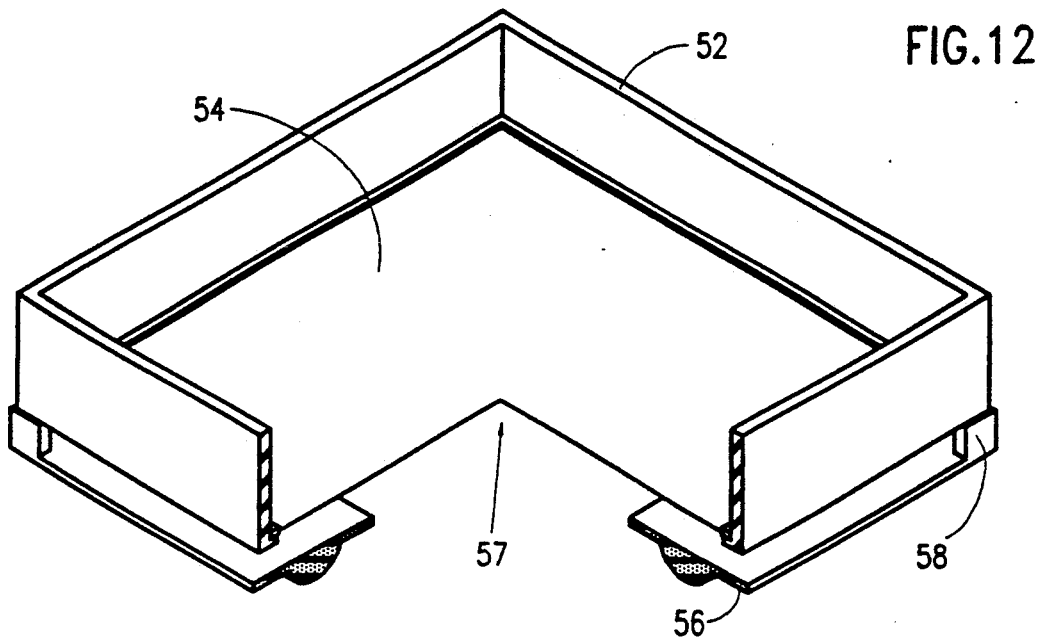
FIGS. 12, 13 and 14 are simplified illustrations of plant growth apparatus constructed and operative in accordance with a preferred embodiment of the present invention.
Figure 13:
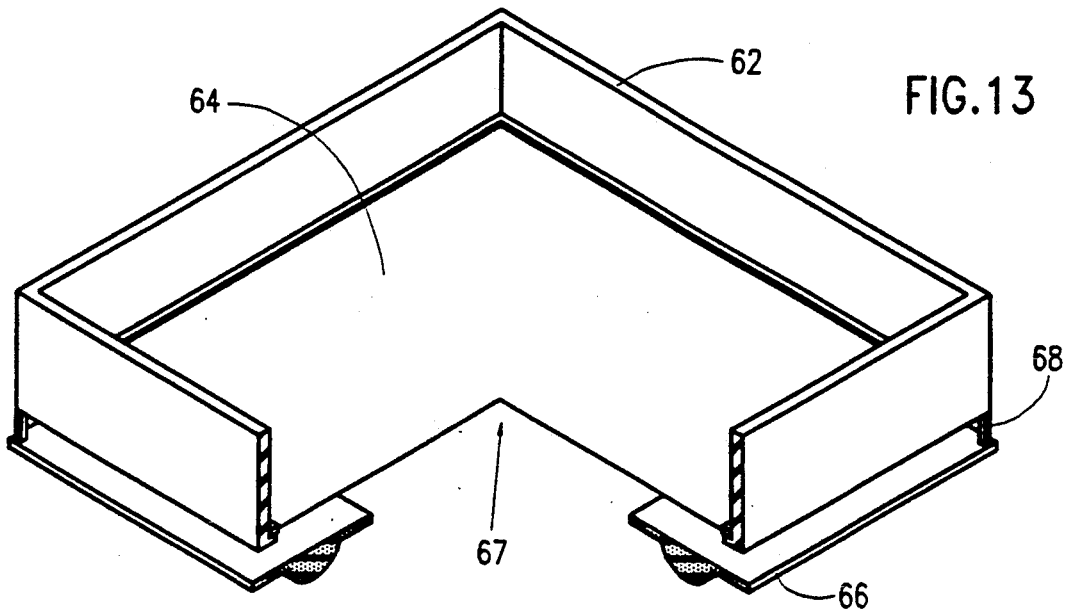
Figure 14:
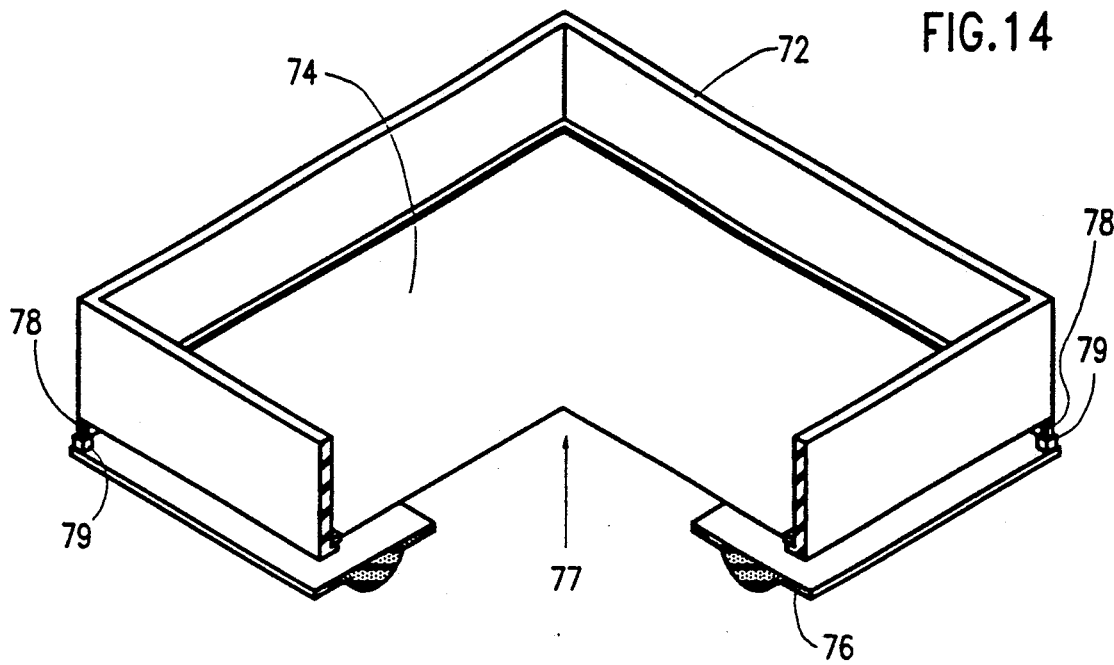

Reference is now made to FIGS. 12-14 which illustrate three alternative structures which exemplify plant growth apparatus constructed and operative in accordance with a preferred embodiment of the present invention.

As illustrated in FIG. 12, the plant growth apparatus comprises an enclosure 52 having a porous bottom surface 54 formed of a membrane such as that described in Example I hereinabove. The enclosure 52 is removably supported on a buoyant element 56 having an aperture 57 and having integrally formed therewith corner elements 58 defining spacers. The enclosure 52 is supported on elements 58 and thus spaced from the remainder of the buoyant element 56.

As illustrated in FIG. 13, the plant growth apparatus comprises an enclosure 62 having a porous bottom surface 64 formed of a membrane such as that described in Example I. The enclosure 62 is removably supported on a buoyant element 66 having an aperture 67. Here the enclosure 62 has integrally formed therewith a plurality of spacers 68. The enclosure 62 is supported on spacers 68 and thus spaced from the buoyant element 66.

Reference is now made to FIG. 14 which illustrates plant growth apparatus comprises an enclosure 72 having a porous bottom surface 74 formed of a membrane such as described hereinabove in Example I. The enclosure 72 is removably supported on a buoyant element 76 having an aperture 77. Here both the enclosure 72 and the buoyant element 76 have integrally formed therewith a plurality of spacers 78 and 79 respectively. The enclosure 72 is supported on spacers 78 and 79 respectively in which spacer 78 fits into a recess in spacer 79 and thus is spaced from the buoyant element 76.

Figure 15:
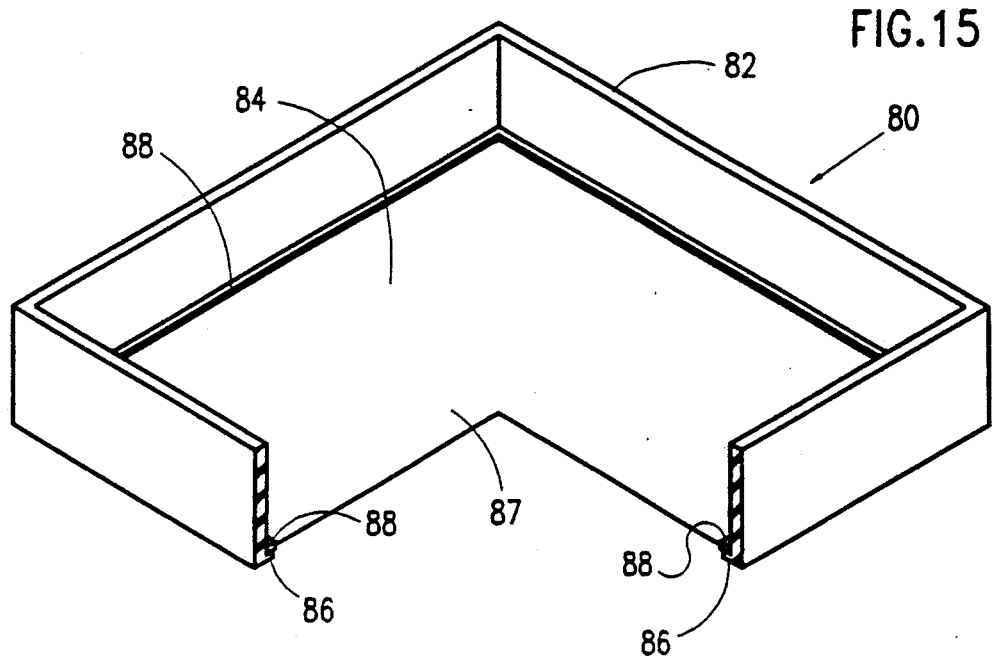
FIG. 15 is a simplified illustration of part of the plant growth apparatus of FIGS. 12, 13 and 14.

FIG. 15 illustrates a preferred embodiment of enclosure 80 in which the side walls 82 are separate from the bottom surface 84. In this preferred embodiment, the side walls 82 are formed as an integrally formed rectangular unit having a peripheral inward facing ledge 86. The bottom surface is defined by a membrane 87, such as described hereinabove in Example I which is supported on a frame 88. Frame 88 rests on peripheral ledge 86.

Reference is now made to FIGS. 16A - 16E, which illustrate a technique for plant growth in accordance with a preferred embodiment of the present invention.

Figure 16A:
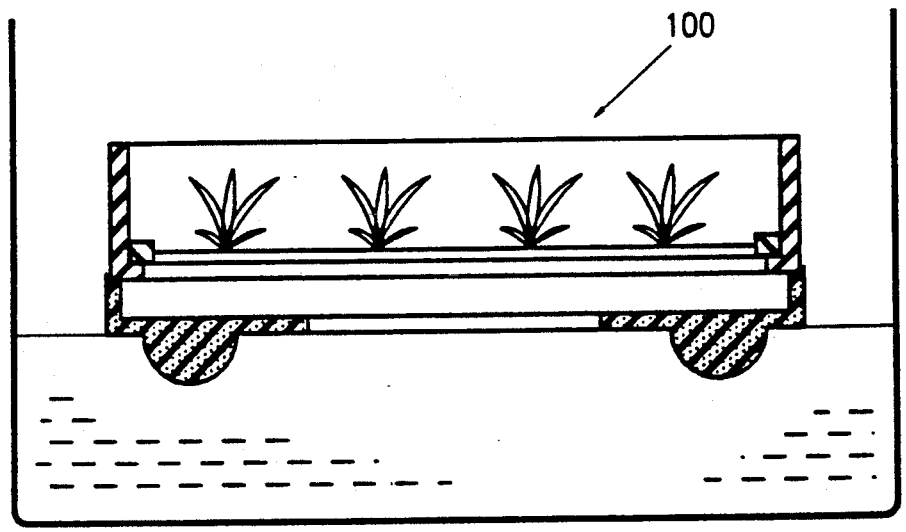
FIGS. 16A, 16B, 16C, 16D and 16E are illustrations of various stages in a plant growth technique in accordance with a preferred embodiment of the present invention.

Initial steps include placing plant material in a plant growth enclosure assembly 100 having a bottom surface formed of a porous material and a buoyant element, such as the enclosure assemblies of any of FIGS. 12–14. The plant growth enclosure may be placed on a body of liquid, as illustrated in FIG. 16A.

Figure 16B:
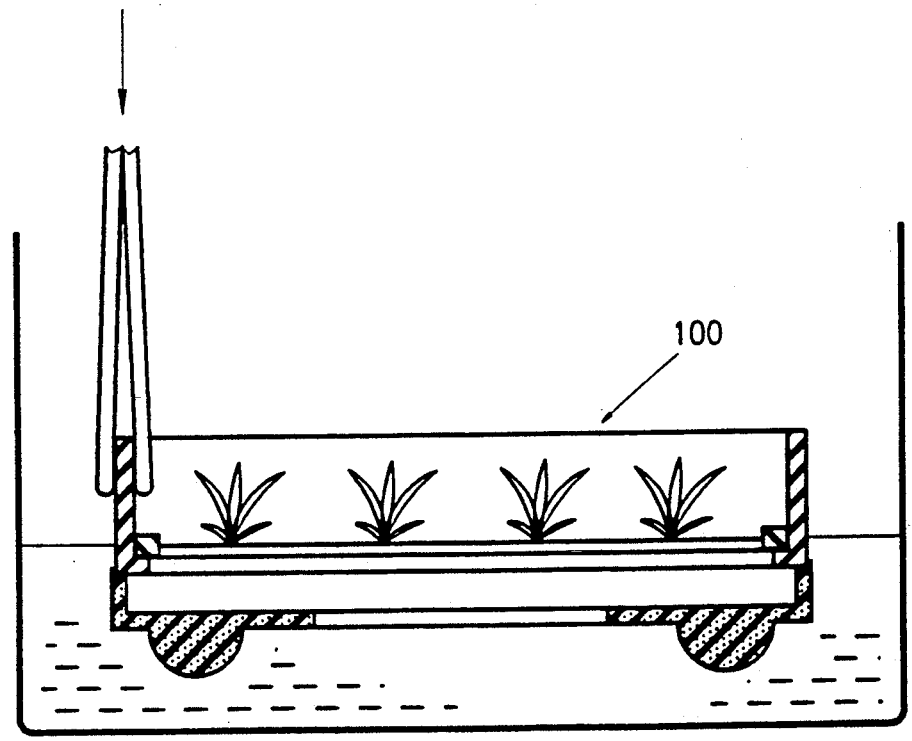

Thereafter, the plant growth enclosure assembly is forced downwardly into the body of liquid such that the porous material at the bottom surface of the enclosure assembly 100 is wetted, as illustrated in FIG. 16B.

Figure 16C:
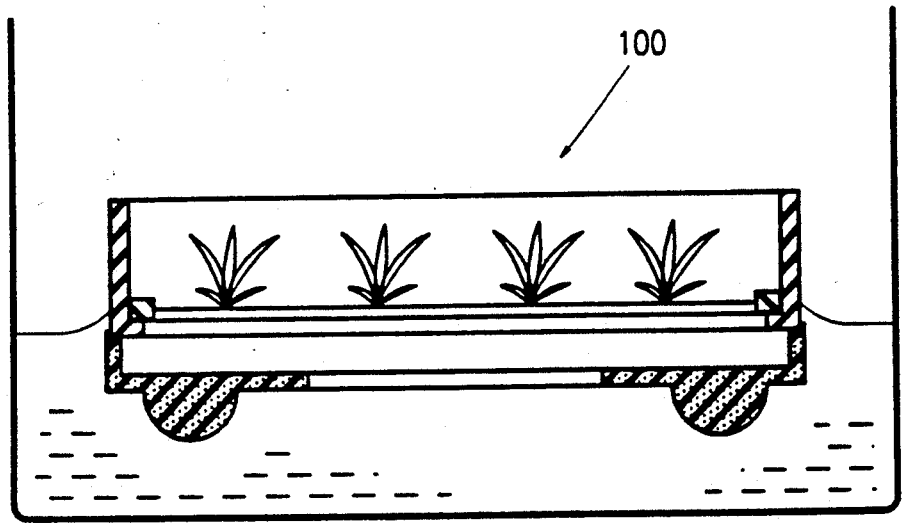

The plant growth enclosure assembly 100 is then allowed to rise partially out of the body of liquid such that the porous material lies above an upper surface of the body of liquid but remains in contact with the upper surface of a meniscus of the body of liquid, as seen in FIG. 16C.

Figure 16D:
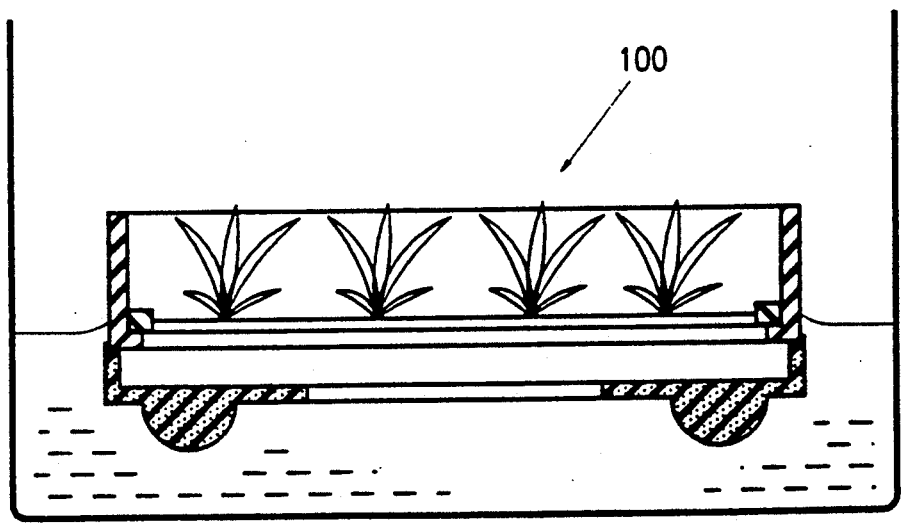
Figure 16E:
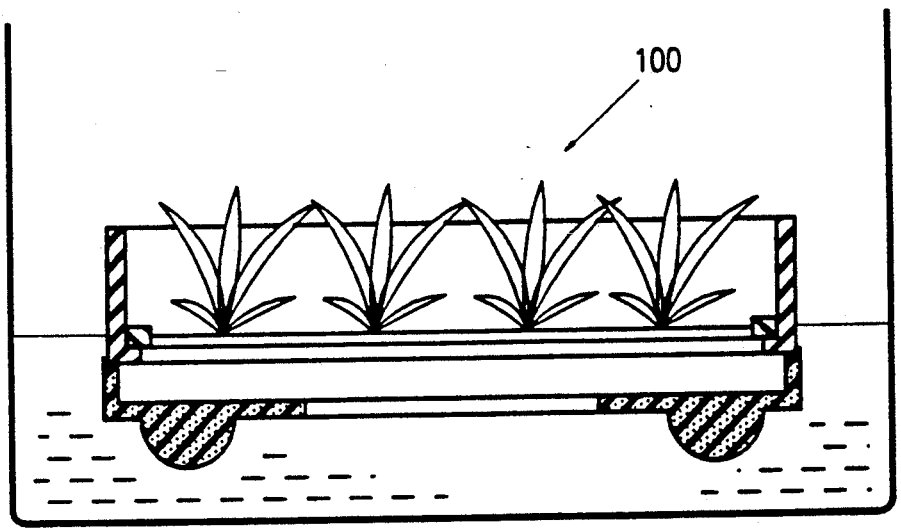

Subsequent growth of the plants in enclosure assembly 100 causes the assembly 100 to move lower in the body of liquid, as seen in FIG. 16D and FIG. 16E. In accordance with a preferred embodiment of the present invention, the buoyant element is sufficiently buoyant to keep the porous material from being flooded at all stages of growth of the plant material in the plant growth enclosure.

It will be appreciated by persons skilled in the art that modifications may be made in the invention without departing from the spirit thereof.

What is claimed is:

1. Apparatus for plant cell tissue culture including:
a plant growth enclosure having a bottom surface formed of a porous material;
a buoyant element, separate from the plant growth enclosure and arranged to be placed thereunder in a body of liquid for supporting the plant growth enclosure; and
spacer apparatus associated with at least one of the plant growth enclosure and the buoyant element for maintaining a predetermined vertical separation between the buoyant element and the porous material and defining a vertical gap between the enclosure and the buoyant element operative to prevent air from being trapped below the porous material wherein, after the porous material is forced into the body of liquid such that it is wetted, the plant growth enclosure rises partially out of the body of liquid such that the porous material lies above an upper surface of the body of liquid but remains in contact with the upper surface of a meniscus of the body of liquid.

2. Apparatus according to claim 1 and wherein said spacer apparatus is integrally formed with the buoyant element.

3. Apparatus according to claim 1 and wherein said spacer apparatus is integrally formed with the enclosure.

4. Apparatus according to claim 1 and wherein said spacer apparatus is partially defined by both the buoyant element and the enclosure.

5. A technique for plant growth including the steps of:
placing plant material in an apparatus according to claim 1 having a bottom surface formed of a porous material and a buoyant element;
placing the apparatus on a body of liquid for supporting the apparatus;
forcing the apparatus into the body of liquid such that the porous material is wetted; and
allowing the apparatus to rise partially out of the body of liquid such that the porous material lies above an upper surface of the body of liquid but remains in contact with the upper surface of a meniscus of the body of liquid.

6. A technique according to claim 5 and wherein said buoyant element is sufficiently buoyant to keep the porous material from being flooded at all stages of growth of the plant material in the apparatus.

7. Apparatus according to claim 1 and wherein said buoyant element is sufficiently buoyant to keep the porous material from being flooded at all stages of growth of the plant material in the plant growth enclosure.

8. Apparatus according to claim 1 and wherein said plant growth enclosure comprises a separate side wall element and a separate porous bottom surface element.

9. Apparatus according to claim 8 and wherein said bottom surface element is supported on said wall element and removable therefrom.

10. Apparatus for plant cell tissue culture comprising:
a container for plant tissues including a frame defining a base and side wall means, a porous material arranged at said base and containing a multiplicity of pores allowing the free diffusive flow of water and other dissolved species; and
flotation means associated with said frame by way of a spacer wherein a vertical gap is maintained between said flotation means and said frame and being operative such that absent the application of an external force, and when said porous material is not wetted, the container will float on an aqueous surface without the porous material touching the surface, and when said porous material is wetted, the porous material base of the device remains in fluid communication with the aqueous surface.

11. Apparatus according to claim 10 and wherein said container and means of flotation are constructed such that when said porous material is wetted, a force in excess of 0.01 dynes/sq.cm. is required in order to lift the base out of fluid engagement from the surface of tissue culture medium.

12. Apparatus according to claim 10 and also comprising divider means disposed to divide the container into a plurality of cells, each communicating with a portion of said porous material and each being suitable for growing a single plant.

13. Apparatus according to claim 10 and wherein said flotation means is removably attached to the frame.

14. Apparatus according to claim 1 and wherein said porous material comprises a microporous polyolefin film of largest estimated pore size between 0.2 and 0.5 microns.

15. Apparatus according to claim 1 and wherein said porous material comprises a polyolefinic nonwoven fabric characterized by an air flow of 11-31 Gurley seconds.

16. Apparatus according to claim 15 wherein the polyolefinic nonwoven fabric has been uniformly needlepunched to produce a multiplicity of pores whose pore size lies between 25 microns and 2000 microns.

17. Apparatus according to claim 1 and wherein the porous material contains a multiplicity of pores uniformly distributed over the surface, whose pore size distribution lies in the range between 0.02 microns and 10 microns.

18. Apparatus according to claim 1 and wherein said porous material is characterized by a bimodal distribution of pores uniformly divided over the surface, whose lower pore size distribution lies in the range between 0.02 microns and 10 microns, and with a second distribution lying between 11 microns and 2000 microns.

19. Apparatus according to claim 12 wherein said porous material also contains a multiplicity of pores uniformly distributed over the surface, whose pore size distribution lies in the range between 0.02 microns and 10 microns, and whose surface contains an additional multiplicity of pores lying in the range of 25 microns to 2000 microns, only on those portions of the surface corresponding to the said cells.

20. Apparatus according to claim 12 wherein said porous material contains perforations which are congruent with said divider means.

21. Apparatus according to claim 19 wherein said porous material contains perforations which are congruent with said divider means.

22. Apparatus according to claim 12 in which the divider means define sharp edges on their face adjacent to the porous material, for cutting the porous material upon application of sufficient force.

23. A method of variably adjusting the amount of fluid fed to plant cells growing on the porous material of any of the preceding claims via adjustment of (a) the flotation force which is in excess of the original displacement weight of the raft and (b) the hydraulic permeability of the porous material.

24. A technique for plant growth including the steps of:

placing plant material of weight X in an apparatus according to claim 1 of weight Y having a bottom surface of surface area A formed of a porous material which a hydrophilic surface and a buoyant element having a buoyancy of Z where $Z>X+Y$;

placing the apparatus on a body of liquid for supporting the apparatus, the body of liquid having a force of adhesion per unit area to the surface of the porous material is B, where $$Z-(X+Y)<A \times B$$

forcing the apparatus into the body of liquid such that the porous material is wetted; and releasing the apparatus and allowing it to rise partially out of the body of liquid such that the porous material lies above an upper surface of the body of liquid but remains in contact with the upper surface of a meniscus of the body of liquid.

25. Apparatus for plant growth including:

a plant growth enclosure assembly of weight Y having a bottom surface of surface area A formed of a porous material with a hydrophilic surface supported by a buoyant element having a buoyancy of Z where $Z>X+Y$ and XD is the weight of plant material placed in the plant growth enclosure, wherein the bottom surface is separated vertically from the buoyant element by a spacer element;

a body of liquid for supporting the plant growth enclosure, the body of liquid having a force of adhesion per unit area to the surface of the porous material is B, where $$Z-(X+Y)<A \times B$$

wherein, after the porous material is forced into the body of liquid such that it is wetted, the plant growth enclosure rises partially out of the body of liquid such that the porous material lies above an upper surface of the body of liquid but remains in contact with the upper surface of a meniscus of the body of liquid.

* * * * *